(12) United States Patent
Takada

(10) Patent No.: US 6,315,713 B1
(45) Date of Patent: Nov. 13, 2001

(54) PROPELLANT SUPPORT APPARATUS FOR SELF-PROPELLED COLONOSCOPE

(76) Inventor: Masazumi Takada, 622-26 Takatsukashinden, Matsudo-city, Chiba, 270-2222 (JP)

( * ) Notice: Subject to any disclaimer, the term of this patent is extended or adjusted under 35 U.S.C. 154(b) by 0 days.

(21) Appl. No.: 09/444,372

(22) Filed: Nov. 22, 1999

(30) Foreign Application Priority Data

Dec. 3, 1998 (JP) .................................................. 10-358411
Apr. 7, 1999 (JP) .................................................. 11-099599

(51) Int. Cl.[7] ............................................................ A61B 1/00
(52) U.S. Cl. .......................................... 600/114; 604/271
(58) Field of Search ............................ 600/114; 604/271, 604/264, 265, 95.03

(56) References Cited

U.S. PATENT DOCUMENTS

| | | | |
|---|---|---|---|
| 3,805,770 | * | 4/1974 | Okada ........................................ 128/4 |
| 4,167,939 | * | 9/1979 | Storz .......................................... 128/4 |
| 4,332,242 | * | 6/1982 | Chikama .................................... 128/3 |
| 5,249,568 | * | 10/1993 | Brefka et al. ............................. 128/3 |
| 5,941,815 | * | 8/1999 | Chang ..................................... 600/114 |

FOREIGN PATENT DOCUMENTS 8-38416   2/1996 (JP) .

* cited by examiner

*Primary Examiner*—Linda C. M. Dvorak
*Assistant Examiner*—Jocelyn Debra Ram
(74) *Attorney, Agent, or Firm*—Young & Thompson

(57) ABSTRACT

A propellant support apparatus to help a self-propelled colonoscope in its smooth insertion, said colonoscope being insertable in the colon of a patient by driving a plurality of endless belts, mounted along the flexible section of an insertion tube of the colonoscope, without causing pain to the patient even at initial insertion of the colonoscope, comprising an insertable anal pipe (1) that has a smooth outer surface and a high frictional inner surface. By using motive force produced by friction between the high frictional inner surface (3) of the insertable anal pipe (1) and the outside circles of endless belts (23), mounted along an insertion tube (21) of the colonoscope, the propellant support apparatus helps the insertion tube (21) to propel forward, without causing damage to the inside wall of the anus, whereby the colonoscope can be inserted into the colon smoothly.

3 Claims, 3 Drawing Sheets

PROPELLANT SUPPORT APPARATUS FOR SELF-PROPELLED COLONOSCOPE

BACKGROUND OF THE INVENTION

The present invention relates to a propellant support apparatus, which helps a self-propelled colonoscope to move forward in a patient's colon. More particularly, it relates to a propellant support apparatus, which is used to propel a self-propelled colonoscope, insertable into the colon, in a self-propelling manner, by driving a plurality of endless belts, mounted along the outside of the flexible section of the insertion tube of the colonoscope.

A colonoscope which does not cause pain to a patient and is capable of smooth insertion into the colon during colono-endoscopic examination has been sought. As such an endoscope, a colonoscope insertable, in a self-propelling manner, along the inside surface of the colon has been provided.

The inventor of the present invention disclosed in Japanese Patent Laid-open No.8-38416 an endoscope capable of self-propelling in the colon of a patient, by driving a plurality of endless belts, mounted along the outside of the flexible section of an insertion tube thereof.

The disclosed colonoscope is provided with a plurality of endless belts along the substantially entire length of the outside surface of the flexible section of the insertion tube thereof.

Each of the endless belts is preferably made of a flexible, strong and optimally adhesive material to be self-propelled along the wall of the colon. As a suitable material, a carbon fiber, synthetic fiber, metallic fiber or rubber may be preferable. The surface of each of the endless belts, made of the material mentioned above, may be preferably coated with an adequately adhesive material to get more adhesion.

And, the adequate adhesion of the endless belts is available to prevent a little loosened endless belts from running idle.

The endless belt are driven by a driving means mounted at the driving section of the colonoscope, and the outside circles of the endless belts contact the wall of the colon, so that frictional force between the colon wall and said endless belts will allow the distal end of the colonoscope to move spontaneously forward through the colon. The inside circle of each of the endless belts passes through one of guide pipes, provided in the flexible section of the insertion tube, leads to the distal end of the flexible section of the insertion tube, and comes out to the outside surface of the insertion tube again, whereby the endless belts rotate endlessly. Consequently, contacting the colon wall, the colonoscope can move spontaneously forward in the colon without excessive extending or bending the colon, which may be caused by pushing a conventional endoscope into the colon. That is, the self-propelled colonoscope is smoothly insertable into the colon, keeping the position and shape of the colon in physiological conditions, so that little pain may be caused to the patient.

The insertion tube of the colonoscope comprises a distal section having a length of about 1 to 2 cm, a bending section having a length of about 10 cm, and a flexible section extending from the flexible section to an operating section thereof. The distal section and the bending section are not provided with the endless belts so that the bending section can bend upwardly and downwardly, right and left, or obliquely on insertion.

Upon insertion of a colonoscope into to the colon, the insertion tube thereof is inserted through the anus, which is a narrow canal and about 5 cm in length, then into the rectum, and further into the sigmoid colon. The whole length of the rectum is about 20 to 21 cm. Since the end portion of the rectum, 14 to 15 cm long, is ampullar, at this end portion, the insertion tube and the endless belts hardly contact the colon wall.

On the other hand, a colonoscope can be manually inserted into the colon, without causing pain to a patient, up to a 25 cm site from the outlet of the anus, which is the same as the total length of the anus and the rectum. Accordingly, the self-propelled colonoscope can be manually inserted into the colon for about 25 cm from the outlet of the anus, and then can be self-propelled by driving the endless belts. However, when the endless belts are started to drive, a portion where the endless belts contact is only 5 to 7 cm, which is the length from the outlet of the anus to around the outlet of rectum.

When the endless belts of a self-propelled colonoscope are started to drive, because of no endless belts provided at a portion of 12 cm from the distal end of the colonoscope, a length of only about 13 cm is allowed for insertion of the endless belts into the anus and the rectum. Thus the insertion tube may not be insertable into the colon smoothly, or the excessive friction between the insertion tube and the walls of the anus and the rectum causes pain to the patient or bleeding.

SUMMARY OF THE INVENTION

In view of above problems, it is an object of the invention to provide a propellant support apparatus for a colonoscope which is insertable in the colon, in a self-propelling manner, by driving a plurality of endless belts, mounted at the outside surface of the flexible section of an insertion tube of said colonoscope, whereby the colonoscope can be inserted into the colon smoothly without causing pain to the patient and bleeding even at an initial insertion.

According to a first aspect of the present invention, a propellant support apparatus comprises an insertable anal pipe that has a smooth outer surface and a high frictional inner surface.

This propellant support apparatus will be used as follows. That is, before insertion of a self-propelled colonoscope into the colon of a patient, the inside of the anus is well observed with an anus mirror. Then, the rectum is expanded with air, after a rectum mirror is inserted into the rectum, to be well observed for safe insertion of the insertable anal pipe therein. The insertable anal pipe is placed at the anus, and the self-propelled colonoscope is manually inserted, through the insertable anal pipe, into the colon. When the insertion tube of the colonoscope is inserted for 25 cm and the distal end of the colonoscope reaches at the sigmoid colon, further to the rectum, the endless belts start to drive. The endless belts further move forward into the sigmoid colon by frictional force between the endless belts and the inner surface of the insertable anal pipe, as well as frictional force between the endless belts and the rectum. When a portion of the insertion tube, at which the endless belts are mounted, contacts the inside surface of the rectum and the sigmoid colon as to be self-propelled, the insertable anal pipe will be removed. Afterward, the colonoscope may be self-propelled by the motive force produced by friction between the endless belts and the inner wall of the colon.

At the beginning of driving the endless belts, the motive force produced by friction between the outside surface of endless belts and the inner surface of the insertable anal pipe, said surface having a high frictional resistance, propels the endless belts, without causing damage to the inside wall of the anus and bleeding at the wall of the rectum, whereby the colonoscope can be inserted into the colon smoothly.

In the propellant support apparatus for a self-propelled colonoscope according to the present invention, the insertable anal pipe thereof can be preferably divided into halves at the plane substantially parallel to the axis. Because, said insertable anal pipe may be pulled out of the anus and removed after the colonoscope is inserted into the colon suitably. That is, the inner surface of said insertable anal pipe has such a high frictional resistance that friction between the inner surface of said insertable anal pipe and the endless belts may become excessively strong, if the insertable anal pipe is kept placed at the anus. Consequently, as the motive force of the insertion tube produced by friction becomes too strong, the insertion tube may be forcefully inserted. In this condition, the wall of the colon will be extended, but not so much as by prior colonoscopes. To avoid such extension of the colon, the propellant support apparatus is to be removed completely, so the motive force of the colonoscope decreases. At that time, said insertable anal pipe is dividable into halves so that it may be easily removed from the insertion tube of the colonoscope after being pulled out of the anus.

The diameter of the insertable anal pipe is preferably 1 to 3 cm and its length is 5 to 20 cm. It is said that a patient feels no pain around the anus when anything having a diameter of 2 cm and a length of 25 cm is inserted. Therefore, insertion of anything having the mentioned-above sizes, enough to get the initial motive force of the colonoscope, causes little pain.

BRIEF DESCRIPTION OF THE DRAWING

FIG. 4 shows an insertable anal pipe according to another embodiment of the present invention.

DETAILED EMBODIMENTS OF THE INVENTION

Referring to the attached drawings, the detailed embodiments of the present invention will be set forth.

Figure 1:
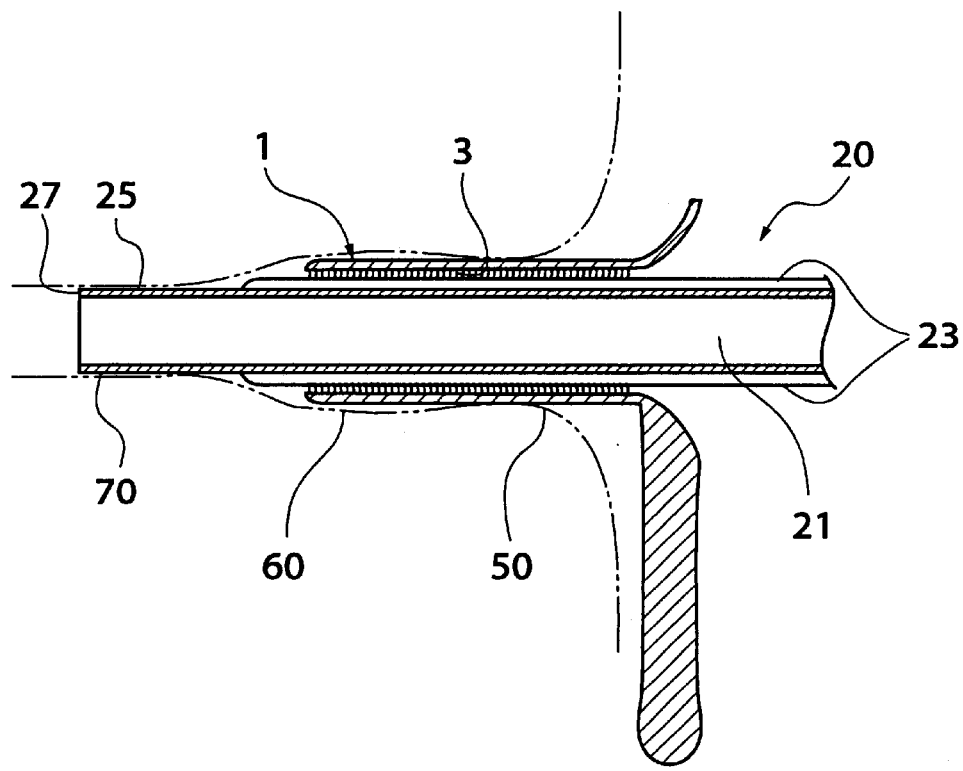
FIG. 1 shows a sectional view of the anus and its vicinity, wherein a colonoscope is inserted through an insertable anal pipe, being placed at the anus, according to one embodiment of the present invention.

FIG. 1 shows a sectional view of the anus and its vicinity, wherein the colonoscope is inserted through the insertable anal pipe, being placed at the anus, according to one embodiment of the present invention.

An insertable anal pipe 1 is made of the material that has a smooth surface, such as stainless steel. Said pipe 1, a hollow sleeve whose section is a circle, has a cylindrical part 5, whose entire length, from the front end to the rear end, has the same diameter and a bottom part 7 that flares. The inner surface 3 of said pipe 1 is so formed to have a high frictional property. The detail of the property will be described later.

The insertable anal pipe 1 is placed by pushing the distal end thereof into the colon, with the rear end being located at the outlet of the anus 50.

The insertion tube 21 of a colonoscope 20 is inserted through the rear end of the insertable anal pipe 1, and is manually pushed up to a position of 25 cm from the outlet of the anus along the inner surface of the insertable anal pipe. Then, the distal end of the insertion tube 21 reaches the starting section of the rectum 60. Under this condition, when endless belts 23 are driven, the outside circle of each of the endless belts 23 rubs on the inner surface of the insertable anal pipe 1 and the inner surface of the rectum 60 to produce motive force, so that the distal section 27 of the insertion tube 21 can move forward within the sigmoid colon 70. The insertion tube 21 is further propelled till the endless belts 23, mounted at the outside surface of the flexible section of the insertion tube, contact the inner wall 25 of the sigmoid colon 70. When the outside circles of the endless belts 23 contact the inner wall 25 of the sigmoid colon 70 to allow the insertion tube 21 to be self-propelled by friction with these inside walls, the insertable anal pipe 1 will be removed.

Because the frictional force between the outside circles of the endless belts and the inner surface 3 of the insertable anal pipe 1 is stronger than the frictional force between the outside circles of the endless belts and the inner wall of the rectum, the endless belts will be propelled forcefully, if the insertable anal pipe is kept placed at the anus.

The endless belts advance in a self-propelling manner by the frictional force with the inner wall of the rectum. Therefore, when the endless belts reach a given site to be self-propelled, the insertable anal pipe 1 will be removed.

Figure 2:
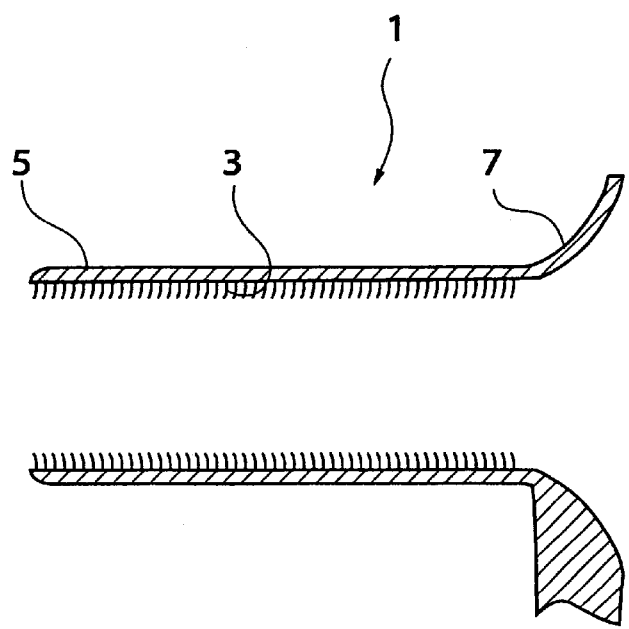
FIG. 2 shows a sectional view of the insertable anal pipe shown in FIG. 1.

FIG. 2 shows a sectional view of the insertable anal pipe shown in FIG. 1.

Figure 3A:
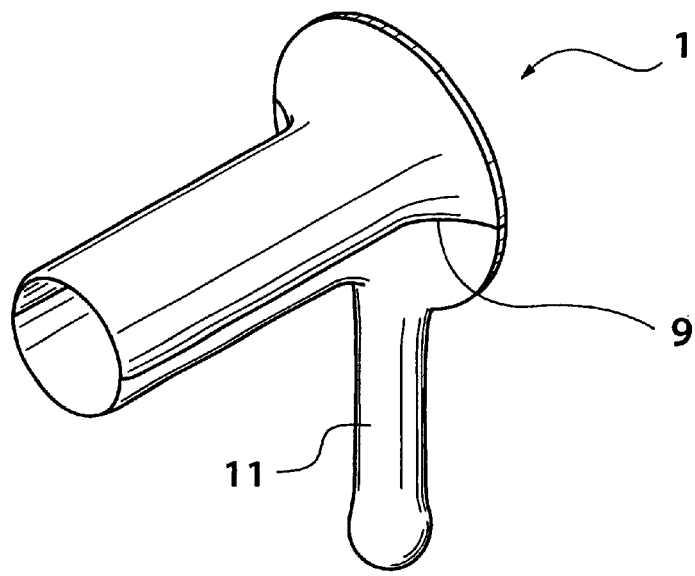
FIG. 3(A) shows a perspective view of the outer appearance of the insertable anal pipe shown in FIG. 1.
Figure 3B:
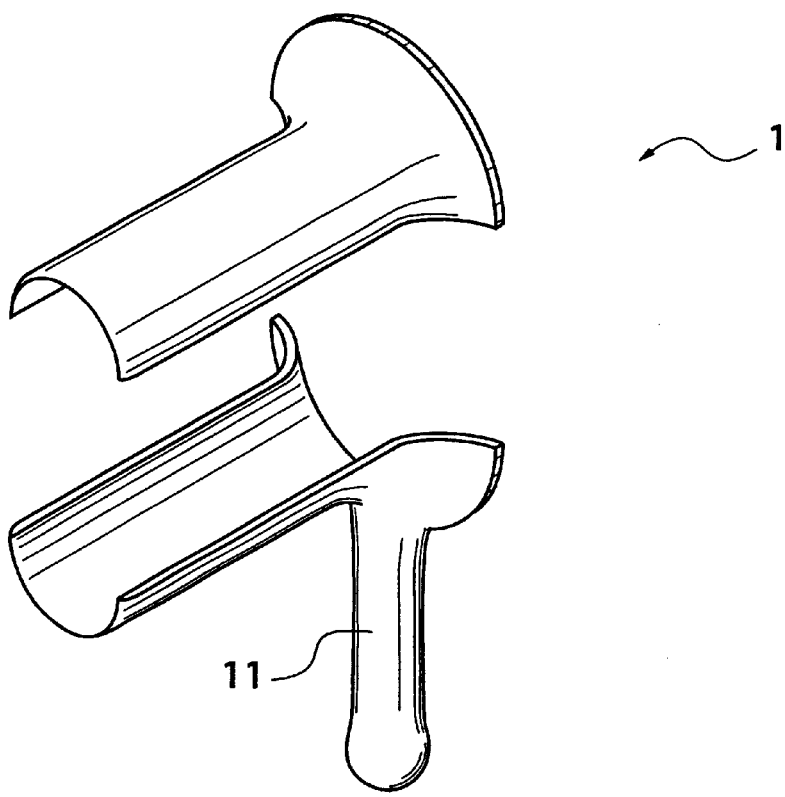
FIG. 3(B) shows a perspective view of the divided insertable anal pipe shown in FIG. 1.

FIG. 3(A) shows a perspective view of the outer appearance of the insertable anal pipe shown in FIG. 1;

FIG. 3(B) shows a perspective view of the divided insertable anal pipe shown in FIG. 1.

The insertable anal pipe 1 comprises the cylindrical part 5, those entire length has the same diameter, and the flared bottom part 7, as mentioned above. The diameter of the cylindrical part 5 is 1 to 3 cm and the length is 5 to 20 cm. Since the inner surface 3 of the cylindrical part 5 is formed as to have a high frictional resistance, or coated with a rubber or hook-loop tape, the motive force produced by frictional force between the endless belts and the insertable anal pipe 1 is stronger than that between the endless belts and the rectum of the same length as the insertable anal pipe. Moreover, as shown in FIG. 3, the insertable anal pipe 1 is dividable into halves at the plane 9 substantially parallel to its axis, so the insertable anal pipe 1 can be removed out of the insertion tube by being horizontally or vertically divided into halves. One of the halves has a handle 11 for easy insertion of the insertable anal pipe 1 into the anus.

Figure 4A:
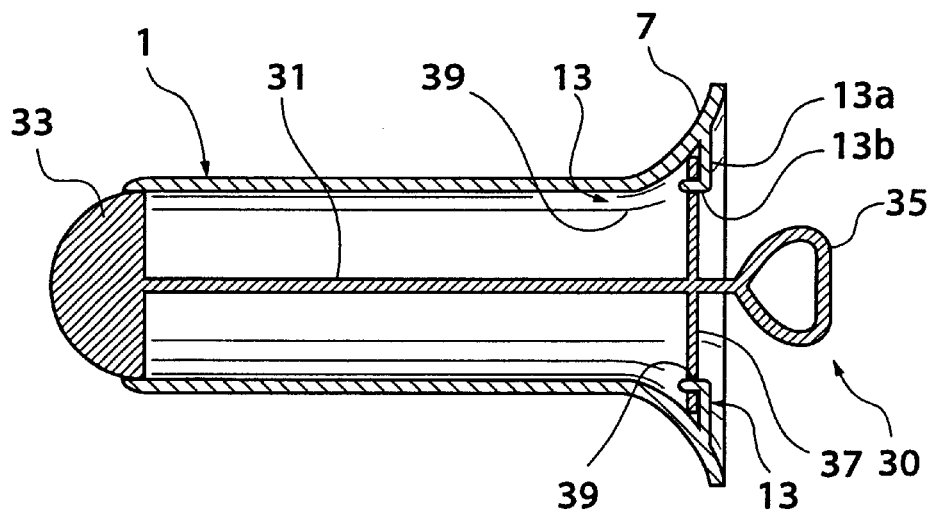
FIG. 4(A) shows a sectional view of the insertable anal pipe.
Figure 4B:
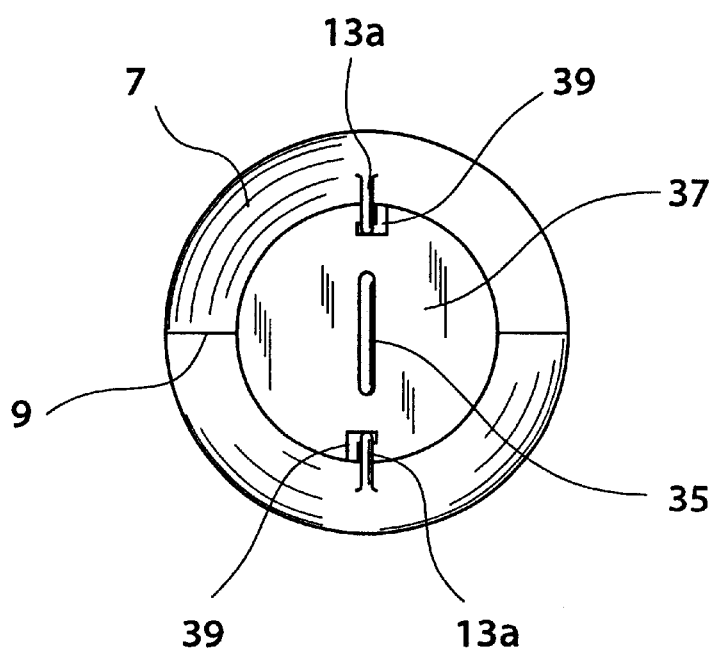
FIG. 4(B) shows a side-sectional view of the insertable anal pipe.

FIG. 4 shows an insertable anal pipe according to another embodiment of the present invention; FIG. 4(A) shows a sectional view of the insertable anal pipe; FIG. 4(B) shows a side sectional view of the insertable anal pipe.

The insertable anal pipe 1, according to the embodiment, is provided with an axis piece 30 to aid the insertable anal pipe, when placed at the anus. The axis piece 30, having a stem 31 provided with a semi-spherical head 33 at the distal end thereof, is inserted into the anus, with being mounted in the insertable anal pipe. The semi-spherical head 33 is disposed protruding from the distal opening of the insertion tube to be smoothly inserted into the anus. After the insertable anal pipe 1 is inserted into the anus, the axis piece is removed. Another end of the axis piece 30 has a handle 35 to attach and detach the axis piece 30 to and from the insertable anal pipe 1.

The inner surface of the bottom part 7 of the insertable anal pipe 1 has L-shaped protrusions 13, oppositely facing. Each of the protrusions 13 comprises a proximal section 13a that extends inwardly from the inner surface of the insertable anal pipe and perpendicularly to axis of the insertable anal pipe, and a distal section 13b that extends axially from the distal end of the proximal section to the distal direction of the pipe.

And, the stem 31 of the axis piece 30 is equipped with an annular flange 37 that flares to a radial direction of the stem. The flange 37 has L-shaped slits 39, each of which is symmetrical with respect to the center of the flange 37. The flange 37, when the axis piece 30 is inserted into the insertable anal pipe 1 in rear, is formed to have a size not to move forward any more, while the annulus of the flange keeps contacting the inner surface of the bottom section 7 of the insertion tube 1. At this time, the substantially entire surface of the semi-spherical head 33 protrudes from the distal end of the insertion tube 1. The proximal section 13a of the protrusion 13, formed at the insertable anal pipe 1, is located at the rear side of the plane, where the flange 37 and the inner surface of the insertion tub 1 are in contact, and the distal section 13b of the protrusion 13 has enough length to pass through the slit 39 of the flange 37.

When the axis piece 30 is mounted to the insertable anal pipe 1, at first the halves of the insertable anal pipe are constructed and then the axis piece 30 is inserted into the constructed insertable anal pipe in rear. Each of the slits 39, formed at the flange 37 of the axis piece 30, being aligned with the proximal end 13a of the protrusion 13, the axis piece 30 is further inserted so that the annulus of the flange 37 will be fixed, contacting the inner surface of the bottom section 7 of the insertable anal pipe 1. And, when the flange 37 is rotated around the axis of the insertable anal pipe 1 with the handle 35, the distal end 13b of the protrusion 13 is to be engaged with the slit 39. Therefore, the axis piece 30 will be fixed at the insertable anal pipe 1, and also each of the dividable halves of the insertable anal pipe 1 will be interconnected.

Under this condition, the insertable anal pipe 1 is inserted up to an adequate position in the anus, and the axis piece 30 is rotated to the other direction as to release the protrusions 13 from the slit 39, and the axis piece 30 will be removed from the insertable anal pipe 1. Then the insertion tube of the colonoscope is inserted into the bore of the insertable anal pipe 1.

When the insertable anal pipe 1 and the axis piece 30 are used, the outer surface of the insertable anal pipe 1 and the distal end 33 of the axis piece 30 may be preferably coated with jelly of narcotics such as Xylocaine Jelly, to carry out easy insertion with less pain.

The above-mentioned insertable anal pipe 1 is preferably removed at the time when the colonoscope reaches a site to move forward in a self-propelling manner, but the colonoscope may be self-propelled, with the insertable anal pipe 1 kept in place. For example, insertion of a colonoscope may cause no pain depending on the shape of the colon. In such a case, the colonoscope may be self-propelled, with the insertable anal pipe kept in place till the distal end of the colonoscope reaches at the deepest section of the colon. When removal of the insertable anal pipe causes the colonoscope not to move forward smoothly through the colon, the insertable anal pipe may be kept in place till the distal end of the colonoscope reaches at the deepest section of the colon.

In light of the above description, the present invention provides a propellant support apparatus for a colonoscope, which is insertable in the colon, in a self-propelling manner, by driving a plurality of endless belts, mounted at the outside surface of the flexible section of an insertion tube of the colonoscope, said propellant support apparatus comprising an insertable anal pipe that has a smooth outer surface and a frictional inner surface.

The motive force produced between the frictional inner surface of the insertable anal pipe and the outside circles of the endless belts will allow the insertion tube of the colonoscope to advance within the colon so that the colonoscope may be smoothly inserted into the colon, without causing damage to the inner wall of the anus. Accordingly, it may be smoothly inserted without causing pain to the patient at the beginning of insertion and also without bleeding at the rectum and the sigmoid colon.

This self-propelled colonoscope is possible to be used for endoscopic examination and treatment of the colon and the entire ileum as well. It may be used, in addition to medical care, by either using the same size or modifying the thickness and length of the self-propelled colonoscope, for conducting inspection of the inside of hot areas such as a nuclear reactor of nuclear power plant and a boiler tube, investigating in remains, searching survivors in earthquake disaster, and conducting inside inspection of machines and buildings, without decomposing or destroying, and it may be further applied to other industrial uses.

While the invention has been particularly shown and described with reference to preferred embodiments thereof, it will be understood by those skilled in the art that various changes may be made therein without departing from the spirit and the scope of the invention.

I claim:

1. A propellant support apparatus for a self-propelled colonoscope, comprising an insertable anal pipe having a smooth outer surface and an inner surface having a higher coefficient of friction than said smooth outer surface.

2. The propellant support apparatus for a self-propelled colonoscope of claim 1, wherein said insertable anal pipe is dividable into halves at a plane substantially parallel to a longitudinal axis.

3. The propellant support apparatus for a self-propelled colonoscope of claim 1, wherein said insertable anal pipe has a diameter of 1 to 3 cm and a length of 5 to 20 cm.

* * * * *